United States Patent
Inomata

(10) Patent No.: US 8,163,472 B2
(45) Date of Patent: Apr. 24, 2012

(54) DRY ANALYTICAL ELEMENT CAPABLE OF REDUCING INFLUENCE OF HEMOLYSIS FOR BODY FLUID COMPONENT MEASUREMENT

(75) Inventor: Hiroko Inomata, Asaka (JP)

(73) Assignee: Fujifilm Corporation, Tokyo (JP)

( * ) Notice: Subject to any disclaimer, the term of this patent is extended or adjusted under 35 U.S.C. 154(b) by 502 days.

(21) Appl. No.: 12/410,788

(22) Filed: Mar. 25, 2009

(65) Prior Publication Data

US 2009/0246817 A1 Oct. 1, 2009

(30) Foreign Application Priority Data

Mar. 26, 2008 (JP) ................................. 2008-081253

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS

| 5,350,675 A | * | 9/1994 | Makino et al. | ................. 435/11 |
| 5,353,794 A | | 10/1994 | Miyazaki | |
| 5,874,229 A | | 2/1999 | Mizutani et al. | |

FOREIGN PATENT DOCUMENTS

EP 1 386 971 A1 2/2004

* cited by examiner

*Primary Examiner* — Sean Aeder
(74) *Attorney, Agent, or Firm* — Birch, Stewart, Kolasch & Birch, LLP

(57) ABSTRACT

It is an object of the present invention to reduce influence of hemolysis in a dry analytical element used for measurement of components in a body fluid sample such as blood. The present invention provides a method for producing a dry analytical element for body fluid component measurement comprising at least a reagent layer containing an $H_2O_2$ color developing reagent and a spreading layer provided on the reagent layer, which comprises steps of providing a spreading layer substrate on the reagent layer containing an $H_2O_2$ color developing reagent and preparing a spreading layer by coating a low-viscosity solution containing oxidase to the spreading layer substrate and then coating a high-viscosity solution containing other reagent components than oxidase thereto.

9 Claims, No Drawings

US 8,163,472 B2

DRY ANALYTICAL ELEMENT CAPABLE OF REDUCING INFLUENCE OF HEMOLYSIS FOR BODY FLUID COMPONENT MEASUREMENT

TECHNICAL FIELD

The present invention relates to a dry analytical element capable of reducing influence of hemolysis for body fluid component measurement, and a method for producing the same.

BACKGROUND ART

At present, a typical reagent system used for a method for measuring a body fluid component (e.g., serum, plasma, or urine) is an oxidizing reagent system in the field of clinical chemistry. In such an oxidizing reagent system, an oxidase, which is selected depending on a predetermined analyte such as cholesterol, reacts with an analyte in the presence of oxygen such that hydrogen peroxide is generated. The generated hydrogen peroxide oxidizes a preferable oxidation/reduction indicator in the presence of a substance having peroxidative activity such that color conversion due to oxidization is observed. Then, the color intensity is measured by visual observation or a measurement device. Thus, the analyte concentration in a body fluid sample can be quantitatively measured.

Measurement is influenced by a negative error due to a reduction action of various body fluid components such as a reducing substance, e.g., ascorbic acid, hemoglobin, erythrocyte catalase, or bilirubin. Also, a pigment such as hemoglobin or bilirubin causes a positive or negative error depending on measurement wavelength. In addition, it has been widely known that absorption by such pigment varies with time during measurement due to influence of light, measurement reagent composition components, and the like. This influences measurement results. Such influence is referred to as "interference."

A variety of methods for reducing interference caused by body fluid components have been studied, regardless of types of measurement methods. For instance, a number of methods, including many methods for reducing interference caused by hemoglobin, have been reported.

JP Patent Publication (Kokai) No. 5-269106 A (1993) discloses a method for reducing interference, which comprises allowing a blood sample to come into contact with an insoluble copper complex containing a high-molecular substance having multiple pendant carboxyl groups and forming an insoluble reaction product with hemoglobin in the blood sample, which can be removed from the blood sample by a solid//liquid separation technique. In addition, JP Patent Publication (Kokai) No. 9-119932 A (1997) describes a finding that temporal changes in the hemoglobin absorption wavelength can be reduced upon optical absorption measurement by setting a measurement wavelength of 517 nm to 529 nm or 580 nm to 592 nm. Based on the finding, the reference discloses a method for reducing such changes in a dry analytical element at a more preferable measurement wavelength of more preferably 520 nm to 526 nm or 583 nm to 589 nm. Further, WO2002/086151 describes that interference caused by hemolyzed hemoglobin can be reduced by addition of at least one or two of thiodiglycol acid, β-thiodiglycol, methionine and the like to a reagent in the measurement of biological components. However, it cannot be said that the above methods sufficiently resolve problems of interference particularly caused by hemolysis observed in a dry analytical element.

DISCLOSURE OF THE INVENTION

It is an object of the present invention to reduce influence of hemolysis in a dry analytical element used for measurement of components in a body fluid sample such as blood.

In order to solve the above object, the present inventors have conducted intensive studies. As a result, they focused on the layer structure of a dry analytical element. Specifically, they have found that the influence of hemolysis can be significantly reduced by separately coating a low-viscosity solution containing an oxidase for the 1st coating and a high-viscosity solution containing other reagent than oxidase for the 2nd coating in the step of coating reagent components to a spreading layer. The above findings have led to the completion of the present invention.

The present invention provides a method for producing a dry analytical element for body fluid component measurement comprising at least a reagent layer containing an $H_2O_2$ color developing reagent and a spreading layer provided on the reagent layer, which comprises steps of providing a spreading layer substrate on the reagent layer containing an $H_2O_2$ color developing reagent and preparing a spreading layer by coating a low-viscosity solution containing oxidase to the spreading layer substrate and then coating a high-viscosity solution containing other reagent components than oxidase thereto.

The present invention further provides a dry analytical element for body fluid component measurement, which is produced by steps of providing a spreading layer substrate on a reagent layer containing an $H_2O_2$ color developing reagent and preparing a spreading layer by coating a low-viscosity solution containing oxidase to the spreading layer substrate and then coating a high-viscosity solution containing other reagent components than oxidase thereto.

Preferably, the viscosity of the low-viscosity solution containing oxidase is 1 mPa·s to 30 mPa·s.

Preferably, the viscosity of the high-viscosity solution containing other reagent components than oxidase is 50 mPa·s to 500 mPa·s.

According to the method of the present invention, influence of hemolysis can be reduced by carrying out multistep coating, involving coating of an oxidase contained in a low-viscosity solution and coating of other reagents than oxidase contained in a high-viscosity solution, to a spreading layer of a dry analytical element. As a result, the accuracy and the precision of body fluid component measurement can be significantly improved. In addition, it is also possible to use a hemolyzed specimen for measurement. Accordingly, there is no need to carry out resampling of blood in order to obtain a nonhemolyzed specimen, resulting in reduction in burdens of patients. It has been known that the degree of hemolysis would vary depending on the technique of the person who collects a blood sample. However, technique-oriented differences would be resolved according to the present invention.

In the cases of dry analytical elements, it is difficult to produce a dry analytical element in which a separation step described in JP Patent Publication (Kokai) No. 5-269106 A (1993) can be carried out. Similarly, it is also difficult to allow such an element to contain a reaction system described in WO2002/086151, in which a sample is first allowed to come into contact with thioglycolic acid or the like in order to reduce the influence of hemoglobin and then subjected to the subsequent reaction. Further, JP Patent Publication (Kokai) No. 9-119932 A (1997) discloses a method for suppressing interference due to the color of hemoglobin in a dry analytical element. In this method, it is impossible to reduce errors due to the reduction of $H_2O_2$ with hemoglobin. In particular, the present invention is characterized in that double-step coating is carried out in order to reduce errors due to reduction of $H_2O_2$ with hemoglobin. Accordingly, effects of suppressing the influence of hemoglobin can be obtained without pretreatment such as separation or pre-reaction.

BEST MODE FOR CARRYING OUT THE INVENTION

The method for producing a dry analytical element of the present invention is characterized by a multistep coating involving coating of an oxidase contained in a low-viscosity solution and coating of other reagent components than oxidase contained in a high-viscosity solution. The terms "low-viscosity solution" and "high-viscosity solution" used herein mean that the viscosity of a liquid containing oxidase is lower than that of a liquid containing other reagent components than oxidase, and that the viscosity of a liquid containing other reagent components than oxidase is higher than that of a liquid containing oxidase, respectively. Both terms refer to a difference between relatively low and high viscosities of two different liquids.

Examples of body fluid that can be used include serum, plasma, and urine. Serum, plasma, urine, or the like can be directly used as a body fluid. Alternatively, a body fluid subjected to an appropriate pretreatment can be used.

The dry analytical element of the present invention is described below. However, the scope of the present invention is not limited to the specific embodiments described below.

The dry analytical element may be structured such that it has at least one reagent layer (referred to as adhesive layer in some cases) and a porous spreading layer on a water-impermeable support.

A fibrous or nonfibrous layer can be used as a spreading layer. A spreading layer functions as a liquid sample spreading layer, and thus it is preferably a layer having a liquid measuring function. A liquid measuring function refers to a function of developing a liquid sample supplied by spotting on the layer surface at an almost constant volume per unit area in the direction parallel to the surface substantially without causing uneven distribution of components of the liquid sample. In order to adjust the spreading area, the spreading rate and the like, a spreading layer can contain a hydrophilic polymer or a surfactant described in JP Patent Publication (Kokai) No. 60-222770 A (1985), JP Patent Publication (Kokai) No. 63-219397 A (1988), or JP Patent Publication (Kokai) No. 62-182652 (1987).

Preferably, a fibrous porous layer (spreading layer) comprises polyester fibers. Typical examples thereof include those described in JP Patent Publication (Kokai) No. 55-164356 A (1980), JP Patent Publication (Kokai) No. 57-66359 A (1982), JP Patent Publication (Kokai) No. 60-222769 A (1985), and the like. Preferably, a nonfibrous porous layer comprises an organic polymer such as polysulfonic acid.

A reagent layer is a layer having a function of bonding the aforementioned water-impermeable support and the spreading layer. The reagent layer may comprise a hydrophilic polymer. Examples of hydrophilic polymers include gelatin and derivatives thereof (e.g., phthalated gelatin), cellulose derivatives (e.g., hydroxypropyl cellulose), agarose, acrylamide polymers, methacrylamide polymers, and copolymers of acrylamide or methacrylamide and various vinyl monomer.

An aqueous solution comprising a hydrophilic polymer is uniformly coated by a well-known method. Publicly known methods can be used for coating. For coating, a dip coating method, an extrusion coating method, a doctor coating method, a hopper coating method, a curtain coating method, or the like can be appropriately selected and used.

It is also possible to coat a spreading layer on a reagent layer. It is preferable to laminate preliminarily supplied knitted fabric or a porous membrane. Bonding can be carried out by a lamination method described in JP Patent Publication (Kokai) No. 55-164356 A (1980). In this method, water is uniformly supplied to the surface of a reagent layer (adhesive layer) comprising a hydrophilic polymer such that the surface becomes wet. A fabric or a porous membrane is laminated thereon via pressurization at a substantially uniform pressure over the entire surface. The thickness of a reagent layer (adhesive layer) is preferably 0.5 to 100 μm and more preferably 1 to 50 μm.

Preferred examples of a material for a light-transmitting support include polyethylene terephthalate, polystyrene, and cellulose ethers such as cellulose triacetate. In order to allow a hydrophilic water-absorbing layer, a detection layer, a substantially nonporous reagent layer or the like to securely adhere to a support, an undercoat layer is generally supplied to a support or a support can be subjected to hydrophilization treatment. The thickness of the support is not particularly limited. However, it is preferably 10 to 1000 μm and more preferably 300 to 800 μm. In the case of a light-transmitting support, final detection can be carried out on either the support side or the spreading layer side. However, in the case of a light-imtransmitting support, detection is carried out on the spreading layer side.

It is also possible to add a stabilizer, a pH buffer, a crosslinking agent (a hardener or a curing agent), a surfactant, a polymer, or the like according to need. They can be contained in a reagent layer or a spreading layer.

Next, the method for producing a dry analytical element capable of reducing influence of hemolysis of the present invention is described below. A reagent composition may be contained in a $1^{st}$ spreading layer or in both a reagent layer and a spreading layer. Alternatively, the entire or substantially entire portion of a reagent composition may be contained in one of the above layers. Alternatively, a reagent composition may be added to a layer that differs from a reagent layer and a spreading layer.

A reagent layer may contain a peroxidase and a chromogen as $H_2O_2$ color developing reagents.

The origin of peroxidase is not particularly limited. However, a horseradish-derived peroxidase or a recombinant peroxidase is preferable. The amount of peroxidase that can be used is preferably approximately 1 to 200 $kU/m^2$ and more preferably approximately 10 to 100 $kU/m^2$.

Examples of a chromogen include 4-aminoantipyrine (4-AA), a phenolic or anilinic Trinder's reagent that develops color as a result of hydrogen-donating coupling, and leuko dye. Preferably, an anilinic reagent can be used as a Trinder's reagent. Examples thereof include N-ethyl-N-sulfopropyl-3-methoxyaniline (ADPS), N-ethyl-N-sulfopropylaniline (ALPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl)-3,5-dimethoxyaniline (DAOS), N-(2-hydroxy-3-sulfopropyl)-3,5-dimethoxyaniline (HDAOS), N-ethyl-N-(2-hydroxy-3-sulfopropyl)-3,5-dimethylaniline (MAOS), and N-ethyl-N-(2-hydroxy-3-sulfopropyl)-3-methoxyaniline (TOOS) (produced by Dojindo Laboratories). The amount of a chromogen that can be used is preferably approximately 0.01 to 10 g/m$^2$ and more preferably approximately 0.05 to 5 g/m$^2$.

A porous spreading layer substrate is coated or laminated on a reagent layer. Then, a reagent is coated to a spreading layer. In the 1$^{st}$ coating step, an oxidase appropriate for a sample to be measured is coated. Examples of such oxidase include, but are not limited to, cholesterol oxidase, glucose oxidase, bilirubinoxidase, xanthine oxidase, amino acid oxidase, fructosyl amino acid oxidase, glutamic acid oxidase, ascorbic acid oxidase, pyruvate oxidase, choline oxidase, glycerophosphate oxidase, alcohol oxidase, and lactate oxidase. In addition, in the case of a sample that does not directly react with oxidase, such as cholesterol ester, it is possible to add cholesterol esterase to a solution containing cholesterol oxidase and coat the resultant. The amount of such an enzyme to be used is preferably approximately 0.1 to 30 kU/1 m$^2$ and more preferably 0.5 to 15 kU/1 m$^2$. In view of permeability into a spreading layer, a low-viscosity solution must be used for coating. Such a solution may be water with a viscosity of approximately 1 mPa·s at 25° C. Further, in view of coating properties, such solution may contain a polymer and a surfactant. A preferable polymer is a low-viscosity polymer with a molecular weight of several tens of thousands. Examples thereof include polyethylene glycol 6000 (molecular weight: 6000) and polyvinyl pyrrolidone Luviskol K17F (BASF). Alternatively, a polymer with a molecular weight of 100,000 or more can be used. For instance, a low-viscosity solution can be prepared by adjusting the concentration of polyvinyl pyrrolidone Kollidon K90F (BASF; molecular weight: 1,000,000 to 1,500,000) or hydroxypropyl cellulose HPC·M (Nippon Soda Co., Ltd., an exclusively disclosed polymer with a viscosity of 150 to 400 mPa·s). In order to facilitate liquid permeation into a spreading layer, the viscosity of a low-viscosity solution containing oxidase is preferably 1 mPa·s to 30 mPa·s, more preferably 1 mPa·s to 25 mPa·s, and further preferably 1 mPa·s to 20 mPa·s. The polymer concentration of the coating solution is preferably 0.1% (wt/wt) to 10% (wt/wt) and more preferably 0.5% (wt/wt) to 5% (wt/wt).

In the 2$^{nd}$ and the following coating steps, the other reagents appropriate for relevant measurement targets (e.g., a surfactant, an antibody, a complex-forming agent, and a polysaccharide) are coated. It might be necessary to subject the components of a sample to be measured to a solubilization step before being subjected to an enzyme reaction. In such case, a high-viscosity solution is used to retain the reagent components in the most possible upper portion of a spreading layer (provided that a surface used for specimen spotting is the upper surface). Preferably, a thickener is a polymer with a molecular weight of 100,000 or more. Examples thereof include polyvinyl pyrrolidone Kollidon K90F (BASF; molecular weight: 1,000,000 to 1,500,000) and hydroxypropyl cellulose HPC·M (Nippon Soda Co., Ltd.; an exclusively disclosed polymer with a viscosity of 150 to 400 mPa·s). In order to retain the reagent in the most possible upper portion of a spreading layer, the viscosity of a high-viscosity solution containing other reagent components than oxidase is preferably 50 mPa·s to 500 mPa·s and more preferably 100 mPa·s to 500 mPa·s. The polymer concentration of a coating solution is preferably 0.1% (wt/wt) to 15% (wt/wt) and more preferably 1% (wt/wt) to 10% (wt/wt).

The other reagent compositions for a dry analytical element may contain at least one additive such as a stabilizer, a pH buffer, a crosslinking agent (a hardener or a curing agent), a surfactant, or a polymer, according to need. Such additives can be contained in a reagent layer and/or a spreading layer of a dry analytical element. A pH buffer can be selected from among those described in references such as "Primary Experimental Methods for Proteins and Enzymes (*Tanpakushitsu/Koso no Kiso Jikken-hou*)" (Takeichi Horio et al., Nankodo Co., Ltd., 1981) and Biochemistry, 5, pp. 467-477, 1966, and Good's Buffers (e.g., MES, TES, HEPES, and MOPS).

The pH of buffer can be determined depending on the optimal pH of an enzyme used and components in a sample to be measured. The pH can be adjusted to preferably 4.0 to 9.0 and more preferably 5.0 to 8.0.

Regarding the method for producing a dry analytical element of the present invention, a highly efficient and uniform production method, comprising a step of coating followed by drying. An example of a production method is described below. A hydrophilic polymer solution containing a color-developing agent and the like is coated to a light-transmitting support, followed by drying. Thus, a reagent layer is obtained. Subsequently, a spreading layer is coated or laminated (by laminating) on the reagent layer. If necessary, a reagent solution is coated onto the spreading layer or it is allowed to permeate into the spreading layer, followed by drying. Thus, a dry analytical element sheet is obtained. The present invention is characterized by the step of coating a reagent to a spreading layer, during which a low-viscosity solution containing oxidase is coated to the spreading layer and dried and then a high-viscosity solution containing other reagent components than oxidase is coated thereto and dried. For dipping a spreading layer, any method can be used, such as a method involving coating, permeation, spraying, or the like. Particularly, coating the reagent is preferred.

Preferably, hot-air drying is carried out for the preparation of a reagent layer and for drying after coating of a reagent to a spreading layer. Drying air is at a temperature of preferably 20° C. to 60° C. and particularly preferably 25° C. to 50° C. Preferably, a dew point is 0° C. to 10° C. Preferably, an air flow is 0.5 to 10 m/second. A required time period for drying is a time period during which a solvent is substantially dried. Meanwhile, drying for a long period of time may result in deactivation of a conjugated enzyme, and thus the time period for drying is preferably 1 to 60 minutes. It is also possible to predetermine preferable drying conditions by controlling the temperature, dew point, air speed, and direction of drying air and a time period for drying in each of a plurality of drying zones.

It is possible to use the dry analytical element of the present invention in a manner such that it is cut into square pieces having sides each approximately 5 mm to 30 mm in length or circular pieces having sizes similar to the sizes of the square pieces, following which the pieces are accommodated in slide frames disclosed in, for example, the following documents so as to be used as chemical analytical slides: JP Patent Publication (Kokoku) No. 57-283331 B (1982); JP Utility Model Publication (Kokai) No. 56-142454 U (1981); JP Patent Publication (Kokai) No. 57-63452 A (1982); JP Utility Model Publication (Kokai) No. 58-32350 U (1983); and JP Patent Publication (Kohyo) No. 58-501144 A (1983). Such embodiments are preferable in view of production, packaging, transportation, storage, measurement operations, and other points. Depending on the purposes for use, the dry analytical element is formed into long tape and such dry analytical element can be used in a state in which it is accommodated in a cassette or a magazine. Alternatively, it can be used in a state in which small pieces thereof are accommodated in a container with an opening or in a state in which small pieces thereof are applied to a card with an opening, for example. Further, cut pieces of the dry analytical element can be directly used.

When the dry analytical element is used, an aqueous liquid sample solution (e.g., a body fluid sample such as blood or urine) in a volume of, for example, approximately 2 μL to 30 μL and preferably 4 μL to 15 μL can be spotted on a porous liquid sample spreading layer. The dry analytical element with spots can be incubated at a constant temperature of approximately 20° C. to 45° C. and preferably approximately at 30° C. to 40° C. for 1 to 10 minutes. The degree of color development or discoloration in the dry analytical element is confirmed by reflectance photometry from the light-transmitting support side, such that the amount of a target substance in a specimen can be determined with the use of a preliminarily prepared calibration curve based on colorimetry principles.

It is very easy to carry out measurement operations with the use of a chemical analyzer described in JP Patent Publication (Kokai) No. 60-125543 A (1985), JP Patent Publication (Kokai) No. 60-220862 A (1985), JP Patent Publication (Kokai) No. 61-294367 A (1986), JP Patent Publication (Kokai) No. 58-161867 A (1983), or the like. Accordingly, quantitative analysis with high precision can be carried out. Depending on purpose and necessary precision level, semiquantitative measurement can be carried out by visually determining the degree of color development.

The dry analytical element can be stored and preserved in a dry state before analysis. Therefore, there is no need to prepare reagents upon analysis. In addition, in general, since a reagent in a dry state has higher stability, the method of the present invention is superior in terms of simplicity and rapidness to a so-called solution method wherein a reagent solution must be prepared upon analysis. Further, the method of the present invention is excellent as a test method whereby a minute amount of a liquid sample can be examined with high precision in a rapid manner.

EXAMPLES

The present invention is hereafter described in greater detail with reference to the following examples, although the technical scope of the present invention is not limited thereto.

Example 1

Production of the Dry Analytical Element of the Present Invention

A gelatin aqueous solution (with the following composition) was coated to a gelatin-undercoated polyethylene terephthalate film 180 μm in thickness which was smooth, colorless and transparent, to a thickness of 15 μm after drying, followed by drying. Thus, a reagent layer was formed.

| | |
|---|---|
| Gelatin | 15.00 g/m$^2$ |
| DAOS (Dojindo Laboratories) | 0.45 g/m$^2$ |
| 4-aminoantipyrine (Wako Pure Chemical Industries, Ltd.) | 0.30 g/m$^2$ |
| Horseradish peroxidase | 30.00 kU/m$^2$ |

Water was supplied over the above film in a volume of approximately 30 g/m$^2$ such that the film became wet. Tricot knitted fabric prepared by knitting (36 gauge) with polyester spun yarn (corresponding to 50 deniers) serving as a spreading layer substrate was laminated thereon via light pressurization, followed by drying. Thereafter, aqueous solutions with the following compositions were separately coated to the above fabric, followed by drying. Thus, a spreading layer was formed.

Composition of the 1$^{st}$ Coating Solution (Viscosity: 4.9 mPa·s)

| | |
|---|---|
| MES Buffer (pH 6.6) | 9.7% (wt/wt) |
| Cholesterol esterase (derived from *Schizophyllum commune*) | 11.0 U/g |
| Cholesterol oxidase (derived from *Pseudomonas* sp.) | 6.7 U/g |
| Pluronic F88 (ADEKA) | 0.76% (wt/wt) |
| Luviskol K17F (BASF) | 2.0% (wt/wt) |

Composition of the 2$^{nd}$ Coating Solution (Viscosity: 259.3 mPa·s)

| | |
|---|---|
| MES Buffer (pH 6.6) | 1.1% (wt/wt) |
| Kollidon K90F (BASF) | 7.3% (wt/wt) |
| EMULGEN B66 (Kao Corporation) | 1.2% (wt/wt) |
| Dextran sulfate (Wako Pure Chemical Industries, Ltd.) | 0.4% (wt/wt) |
| Magnesium chloride hexahydrate (Wako Pure Chemical Industries, Ltd.) | 2.6% (wt/wt) |

The finished product subjected to the above coating was cut into 12-mm square pieces. Each piece was accommodated in a cassette having a specimen spotting portion with a diameter of 10 mm such that a high-density lipoprotein cholesterol (HDL-C) measurement slide was produced.

Comparative Example 1

Production of a Dry Analytical Element for Comparison

The operation step of laminating tricot knitted fabric serving as a spreading layer substrate via light pressurization and drying the resultant was carried out as in Example 1. Then, an aqueous solution having the following composition was coated to the obtained element, followed by drying. Thus, as in the case of Example 1, an HDL-C measurement slide was produced.

Composition (Viscosity: 260.5 mPa·s)

| | |
|---|---|
| MES Buffer (pH 6.6) | 10.8% (wt/wt) |
| Kollidon K90F (BASF) | 7.3% (wt/wt) |
| Dextran sulfate (Wako Pure Chemical Industries, Ltd.) | 0.4% (wt/wt) |
| Magnesium chloride hexahydrate (Wako Pure Chemical Industries, Ltd.) | 2.6% (wt/wt) |
| EMULGEN B66 (Kao Corporation) | 1.2% (wt/wt) |
| Pluronic F88 (ADEKA) | 0.76% (wt/wt) |
| Cholesterol esterase (derived from *Schizophyllum commune*) | 11.0 U/g |
| Cholesterol oxidase (derived from *Pseudomonas* sp.) | 6.7 U/g |

Test Example

Evaluation of Influence of Hemolysis 10 ml of blood (a specimen with an HDL-C concentration of 75 mg/dL) was sampled from a healthy volunteer with the use of a blood sample tube containing heparin lithium as an anticoagulant. 1 ml of the specimen was frozen at −80° C. for 2 hours. Then, the temperature was immediately increased to room temperature so as to cause hemolysis. Thus, hemolyzed plasma was obtained. Meanwhile, the remaining portion (9 mL) was allowed to stand at room temperature for 30 minutes, followed by centrifugation. Thus, plasma was obtained. The hemoglobin concentration of the hemolyzed plasma was measured with a Fuji Dry Chem slide Hb-W, followed by dilution with plasma to a hemoglobin concentration of 500 mg/dL. A plasma sample with a hemoglobin concentration of 0 mg/dL containing no hemolyzed plasma and a plasma sample with a hemoglobin concentration of 500 mg/dL were each spotted (10 µl each) on a separate HDL-C measurement slide produced in Example 1. Then, the HDL-C concentration was measured with an FDC7000 Dry Chem analyzer (produced by FUJIFILM Corporation). As shown in table 1, the slide obtained in Example 1 experienced substantially no negative errors caused by hemoglobin.

The plasma sample with a hemoglobin concentration of 0 mg/dL and the plasma sample with a hemoglobin concentration of 500 mg/dL were each spotted on a separate HDL-C measurement slide produced in Comparative Example 1 by carrying out an operation step similar to that used in the above case. As shown in table 1, the slide obtained in Comparative Example 1 experienced a significant negative error caused by hemoglobin.

TABLE 1

| HDL-C concentration change rate upon comparison of the HDL concentration with a hemoglobin concentration of 500 mg/dL and that with a hemoglobin concentration of 0 mg/dL | |
|---|---|
| | HDL-C concentration changed |
| Example 1 | −3% |
| Comparative Example 1 | −94% |

As a result of comparison of the results listed in table 1, it was confirmed that a dry analytical element capable of reducing influence of hemoglobin can be obtained by separately coating two different coating solutions to a spreading layer and distributing oxidase on the reagent layer side.

The invention claimed is:

1. A method for producing a dry analytical element for body fluid component measurement comprising at least a reagent layer containing an $H_2O_2$ color developing reagent and a spreading layer provided on the reagent layer, which comprises steps of:
   providing a spreading layer substrate on the reagent layer containing an $H_2O_2$ color developing reagent;
   coating a low-viscosity solution containing an oxidase on the spreading layer substrate; and
   then coating a high-viscosity solution containing reagent components other than the oxidase on the spreading layer substrate, thereby preparing the spreading layer,
   wherein the viscosity of the low-viscosity solution is 1 mPa·s to 30 mPa·s, and the viscosity of the high-viscosity solution is 50 mPa·s to 500 mPa·s.

2. A dry analytical element for body fluid component measurement, which is produced by the method according to claim 1.

3. The method according to claim 1, wherein the viscosity of the low-viscosity solution is 1 mPa·s to 25 mPa·s.

4. The method according to claim 1, wherein the viscosity of the low-viscosity solution is 1 mPa·s to 20 mPa·s.

5. The method according to claim 1, wherein the viscosity of the high-viscosity solution is 100 mPa·s to 500 mPa·s.

6. The method according to claim 1, wherein the spreading layer substrate is a porous spreading layer substrate.

7. The method according to claim 1, wherein the spreading layer substrate is a tricot knitted fabric.

8. The method according to claim 1, wherein the dry analytical element consists essentially of the reagent layer and the spreading layer.

9. The dry analytical element according to claim 2, wherein said dry analytical element comprises reagent components in the upper most portion of the spreading layer.

* * * * *